US008058411B2

United States Patent
Mundt et al.

(10) Patent No.: US 8,058,411 B2
(45) Date of Patent: Nov. 15, 2011

(54) METHOD FOR PRODUCING MATURE VWF FROM VWF PRO-PEPTIDE

(75) Inventors: Wolfgang Mundt, Vienna (AT); Artur Mitterer, Orth/Donau (AT); Meinhard Hasslacher, Vienna (AT); Christa Mayer, Wolfsthal (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 58 days.

(21) Appl. No.: 12/152,762

(22) Filed: May 16, 2008

(65) Prior Publication Data

US 2009/0029918 A1    Jan. 29, 2009

Related U.S. Application Data

(60) Provisional application No. 60/930,891, filed on May 18, 2007.

(51) Int. Cl.
*C07K 1/18* (2006.01)
*C07K 17/00* (2006.01)
*A61K 35/16* (2006.01)

(52) U.S. Cl. ........ 530/416; 530/350; 530/380; 530/417; 525/54.1; 435/69.6

(58) Field of Classification Search ........................ None
See application file for complete search history.

(56) References Cited

U.S. PATENT DOCUMENTS

| 6,210,929 | B1 | 4/2001 | Schlokat et al. | |
|---|---|---|---|---|
| 2006/0160948 | A1* | 7/2006 | Scheiflinger et al. | ........ 525/54.1 |

FOREIGN PATENT DOCUMENTS

| EP | 0775750 A | 5/1997 |
|---|---|---|
| WO | WO-00/49047 | 8/2000 |

OTHER PUBLICATIONS

Cameron et al., Polyarginines are potent furin inhibitors. *J. Biol. Chem.* 275: 36741-99 (2000).
Leyte et al., The pro-polypeptide of von Willebrand factor is required for the formation of a functional factor VIII-binding site on mature von Willebrand factor. *Biochem. J.* 274: 257-261 (1991).
Molloy et al., Human furin is a calcium-dependent serine endoprotease that recognizes the sequence Arg-X-X-Arg and efficiently cleaves anthrax toxin protective antigen. *J. Biol. Chem.* 267: 16396-402 (1992).
Preininger et al., Strategies for recombinant Furin employment in a biotechnological process: complete target protein precursor cleavage. *Cytotechnology.* 30: 1-15 (1999).
Schlokat et al., Production of highly homogeneous and structurally intact recombinant von Willebrand factor multimers by furin-mediated propeptide removal in vitro. *Biotechnol. Appl. Biochem.* 24: 257-67 (1996).
Takagi et al., A collagen-binding glycoprotein from bovine platelets is identical to propolypeptide of von Willebrand factor. *J. Biol. Chem.* 364: 10425-30 (1989).
Than et al., The endoproteinase furin contains two essential $Ca^{2+}$ ions stabilizing its N-terminus and the unique S1 specificity pocket. *Acta. Cryst.* D61: 505-12 (2005).
International Search Report, International Application No. PCT/US2008/006291, mailed Sep. 1, 2008.
Fischer, "Recombinant von Willebrand factor: Potential therapeutic use," *Journal of Thrombosis and Thrombolysis* 8: 197-206 (1999).
Fischer et al., "Biochemical and functional characterization of recombinant von Willebrand factor produced on a large scale," *Cell. Mol. Life Sci.* 53: 943-950 (1997).

* cited by examiner

*Primary Examiner* — Marsha Tsay
(74) *Attorney, Agent, or Firm* — Marshall, Gerstein & Borun LLP

(57) ABSTRACT

The present invention relates to a method for producing a mature von Willebrand Factor (VWF) from von Willebrand Factor pro-peptide comprising the steps:
  immobilizing VWF pro-peptide on an ion exchange resin,
  incubating the immobilized VWF pro-peptide with furin to obtain immobilized mature VWF, and
  isolating mature VWF from the ion exchange resin by elution.

30 Claims, 2 Drawing Sheets

SEQUENCE LISTING

```
<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Ser Leu Ser Cys Arg Pro Pro Met Val
1               5
```

METHOD FOR PRODUCING MATURE VWF FROM VWF PRO-PEPTIDE

This application claims the priority benefit of U.S. Provisional Patent Application No. 60/930,891 filed May 18, 2007, herein incorporated by reference in its entirety.

FIELD OF THE INVENTION

The present invention relates to methods for producing mature von Willebrand Factor from von Willebrand Factor pro-peptide.

DESCRIPTION OF THE RELATED ART

In the course of protein maturation within a cell the protein to be matured undergoes posttranslational modifications. These modifications include among others acetylation, methylation, glycosylation and proteolytic cleavage. These modifications are in many cases necessary for the protein function and activity and they may also influence the efficiency of proteins, in particular of enzymes.

Pro-proteins (or protein precursors) are inactive proteins that are turned into an active form by one or more of these post-translational modifications, in particular by the cleavage of a pro-peptide from the pro-protein. Examples of pro-proteins include, e.g., pro-insulin, prothrombin etc.

The production of activated proteins is of high clinical and diagnostic importance. For instance, activated or matured proteins may be used to control blood coagulation.

Active proteins are usually available at very low amounts in living organisms. Therefore their pro-proteins and pro-enzymes are preferably activated in vitro by contacting them with activation enzymes (e.g. proteases).

Current methods for producing mature proteins from pro-proteins use either immobilized proteases or are performed in free solution. Both methods have disadvantages. Among these is a requirement that the protease be immobilized following processing.

Von Willebrand factor (VWF) is a glycoprotein circulating in plasma as a series of multimers ranging in size from about 500 to 20,000 kD. Multimeric forms of VWF are composed of 250 kD polypeptide subunits linked together by disulfide bonds. VWF mediates the initial platelet adhesion to the sub-endothelium of the damaged vessel wall; it is thought that only the larger multimers also exhibit hemostatic activity. The multimers having large molecular masses are stored in the Weibel-Pallade bodies of the endothelial cells and liberated upon stimulation. Liberated VWF is then further processed by plasma proteases to result in low molecular weight forms of VWF.

VWF is synthesized by endothelial cells and megakaryocytes as pre-propeptide-VWF ("pp-VWF") that consists to a large extent of repeated domains. Upon cleavage of the signal peptide, VWF pro-peptide dimerizes through disulfide linkages at its C-terminal region. The dimers serve as protomers for multimerization, which is governed by disulfide linkages between the free end termini. The assembly to multimers is followed by the proteolytic removal of the pro-peptide (Leyte et al., Biochem. J. 274 (1991), 257-261.

The physiological role of VWF pro-peptide is postulated to lie in the government of the assembly of VWF multimers, either before or after the cleavage from VWF pro-peptide molecules. (Takagi et al., JBC 264 (18) (1989), 10425-10430. Whereas in humans the removal of the pro-peptide is almost complete, this process is not very efficient in the case of recombinant high-level expression of VWF in mammalian cell lines. Cell culture supernatants from such engineered cell lines generally comprise a mixture of mature VWF and VWF precursors like VWF pro-peptide. In order to obtain mature VWF it is therefore necessary to convert the VWF precursors, in particular VWF pro-peptide, into mature VWF. In EP 0 775 750 A, for instance, this maturation is achieved by using furin. In particular, it is suggested in EP 0 775 750 A to co-express furin and VWF recombinantly so that the maturation of VWF may occur in situ. In WO 00/49047 a method for producing mature VWF using thrombin is described, wherein the maturation is performed in solution or by using thrombin bound on a solid support.

SUMMARY OF THE INVENTION

The present invention provides an efficient method for producing mature von Willebrand Factors (VWF) from VWF pro-peptide. The present invention provides a novel method of producing mature VWF by immobilizing VWF pro-peptide on an ion exchange resin, followed by maturation of the bound VWF pro-peptide with furin and elution of the maturated VWF from the ion exchange resin. The method of the present invention is particularly suited for the in vitro maturation of VWF from VWF pro-peptide. This method allows the production of mature VWF with a high specific activity and purity.

The present invention relates to a method for producing mature VWF from VWF pro-peptide comprising the steps:
immobilizing VWF pro-peptide on an ion exchange resin,
incubating the immobilized VWF pro-peptide with a solution comprising furin to obtain immobilized mature VWF, and
isolating mature VWF from the ion exchange resin by elution.

DETAILED DESCRIPTION OF THE INVENTION

Figure 1:
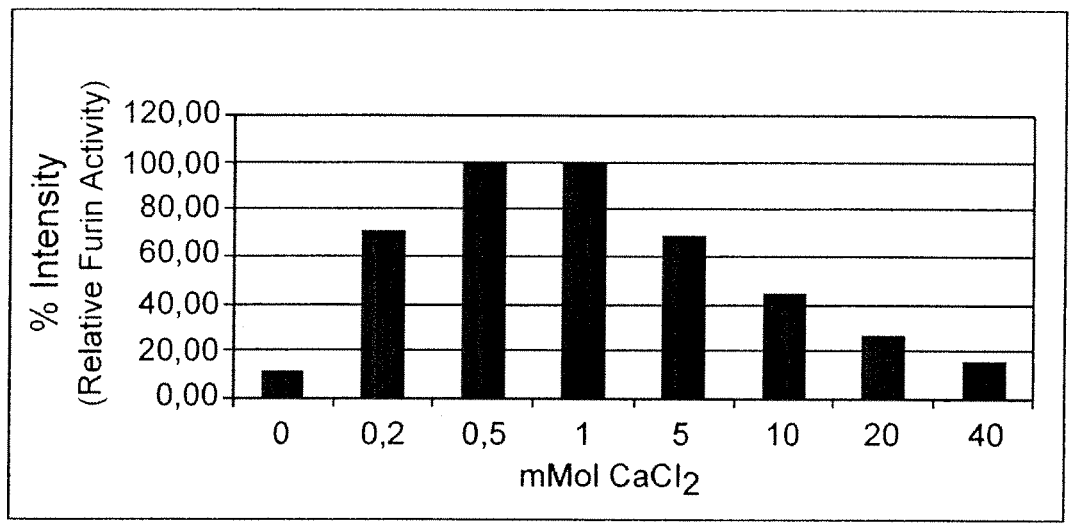
FIG. 1 shows the $Ca^{2+}$ dependence of furin activity.

The present invention relates to a method for producing mature von Willebrand Factor (VWF) from von Willebrand Factor pro-peptide comprising the steps:
immobilizing VWF pro-peptide on an ion exchange resin,
incubating the immobilized VWF pro-peptide with a solution comprising furin to obtain immobilized mature VWF, and
isolating mature VWF from the ion exchange resin by elution.

The method of the present invention is particularly suited for the in vitro maturation of VWF from its VWF pro-peptide form. Current conventional methods produce mature VWF by either incubating its pro-peptide form with proteases in a liquid phase whereby the maturation itself (i.e. the cleavage of the pro-peptide from the pro-protein) occurs in an unbound state in free solution, or as described for example in WO 00/49047, by immobilizing the protease on a solid carrier, which is contacted and incubated with a preparation comprising VWF pro-peptide (see e.g. WO 00/49047). However, these methods have various disadvantages over the method according to the present invention.

Industrially, VWF, in particular recombinant VWF (rVWF), is synthesized and expressed together with rFVIII in a genetically engineered CHO cell line. The function of the co-expressed rVWF is to stabilize rFVIII in the cell culture process. rVWF is synthesized in the cell as the pro-form, containing a large pro-peptide attached to the N-terminus. Upon maturation in the endoplasmatic reticulum and Golgi apparatus, the pro-peptide is cleaved off by the action of the cellular protease furin and is secreted as a homopolymer of identical subunits, consisting of dimers of the expressed protein. However, the maturation is incomplete, leading to a product comprising a mixture of pro-peptide and mature VWF.

Due to the high efficacy of the method of the present invention, the un-maturated VWF pro-peptide expressed during the recombinant synthesis process is substantially entirely converted into mature VWF. A preparation obtainable by this method may comprise at least 90%, more preferably at least 95%, more preferably at least 98%, even more preferably at least 99%, of mature VWF in relation to its VWF pro-peptide form.

It has been shown in previous publications, that VWF pro-peptide can be converted to the mature form by in vitro treatment with furin or furin-like proteases (Schlokat U. et al. (1996) Biotechnol. Appl. Biochem. 24:257-267; Preininger A. et al. (1999) Cytotechnology 30:1-15). Furin belongs to the family of the pro-protein convertases and is dependent on $Ca^{++}$. This enzyme specifically cleaves the C-terminal peptide bond of arginine within a specific sequence, containing arginine at positions −1 and −4. This sequence can be found in numerous human proteins, showing that furin plays a major role in the maturation of a number of human pro-peptide-proteins.

Furin used in the method of the present invention is preferably of recombinant origin. Recombinantly produced proteases are advantageously employed because they can be produced in high quantities.

In contrast to conventional methods, the VWF pro-peptide is immobilized on a solid support (i.e. ion exchange resin) in a way that the mature protein will remain after its maturation reaction immobilized on said support. This has several advantages over the methods known in the art.

The method of the present invention combines a purification step, preferably chromatographic purification step, with the maturation reaction of VWF pro-peptide. Therefore no separate process step to remove the pro-peptide or the protease is required. In contrast thereto, the methods known in the art always required that the maturated protein is further purified either from the protein/protease/pro-peptide mixture or from the protein/pro-peptide mixture. The VWF pro-peptide in the method of the present invention is preferably comprised in the flow-through or removed from the solid support by at least one washing step, whereas the maturated protein remains throughout this process bound to the solid support. Hence, the method of the present invention increases the process economy as compared to methods of the prior art and facilitates the production of a mature protein from its pro-peptide form.

A further advantage of the method according to the present invention is that furin may be obtained from crude cell culture supernatant of a cell line secreting said protease or cell extract. Therefore, no or only partial purification of the pro-protein convertase is required in order to maturate the pro-protein bound on the ion exchange resin.

After the maturation of VWF pro-peptide to mature VWF, the mature protein immobilized on the ion exchange resin may be washed to remove unwanted molecules from the resin. These molecules include the VWF pro-peptide or other proteins and compounds added to said resin during the incubation.

The method of the present invention is terminated when the mature VWF protein is eluted from the ion exchange resin. This is particularly advantageous because it allows the purification of the mature VWF on the ion exchange resin without the necessity of further process steps. It also allows for the addition of washing steps, for example to remove the VWF propeptide, before elution. Thus, the elution in the present method may be achieved using an elution buffer with desired properties and not with a buffer or solution that is required to activate the VWF pro-peptide.

Because VWF pro-peptide can be produced recombinantly in large quantities, it is the preferred source of VWF pro-peptide in the method of the present invention. However, the VWF pro-peptide used in the present invention is not limited solely to that obtained recombinantly. The present method can be used with VWF pro-peptide obtained from any source, including, but not limited to plasma, a plasma fraction and a solution derived therefrom. The VWF pro-peptide to be maturated according to the pre-sent invention may originate from various sources, whereby the VWF may be provided in a purified, partially purified or even unpurified form. If the VWF pro-peptide is provided in a partially purified or unpurified form it has to be considered that some components (impurities) may inhibit or partially inhibit the maturation process.

Since it is preferred to use in the method of the present invention VWF pro-peptide of recombinant origin, the VWF pro-peptide containing solution may be a culture supernatant prepared from a recombinant cell culture. Of course, it is also possible that the source of the VWF pro-peptide of the present invention comprises a partially purified, recombinantly produced VWF pro-peptide, which can be used for maturation.

According to a preferred embodiment of the present invention the ion exchange resin comprises trimethylaminoethyl-groups (TMAE). Other ion exchange resins known in the art that are capable of binding VWF pro-peptide are also suitable.

In order to facilitate the maturation process and to provide VWF pro-peptide immobilized on the resin at an elevated concentration, in one embodiment of the invention, the chromatographic resin is packed in a chromatographic column. Since the concentration of VWF pro-peptide in the course of its in vitro maturation influences the maturation efficiency, it is advantageous to pack the chromatographic resin in a column. Furthermore, the use of chromatographic columns allows the efficient control of the parameters of maturation in a more reproducible manner and makes it simpler to perform the maturation of VWF in vitro.

If VWF pro-peptide is immobilized on an anion exchange resin and incubated with a solution exhibiting VWF pro-peptide convertase activity, the conductivity measured at 25° C. is, in one embodiment of the invention below 25 mS/cm, in another embodiment of the invention below 20 mS/cm, and in another embodiment of the invention below 16 mS/cm.

VWF pro-peptide as well as VWF can be efficiently immobilized on anion exchange resins at these conductivity levels. Consequently the buffers applied in the course of the present method have to be adapted correspondingly.

Mature VWF is eluted from the anion exchange resin at a conductivity, measured at 25° C., of, in one embodiment of the invention, at least 40 mS/cm, in another embodiment of the invention, at least 60 mS/cm, and in another embodiment of the invention, at least 80 mS/cm.

Of course it is possible to apply further washing steps before the mature VWF is eluted from the anion exchange resin.

According to an embodiment of the invention, furin further comprises $CaCl_2$ at a concentration of 0.01 to 10 mM; according to another embodiment, at a concentration of 0.1 to 5 mM; and according to another embodiment, at a concentration of 0.2 to 2 mM.

For their proteolytic activity many proteases need co-factors like bivalent metal ions. Furin requires for its activity calcium ions. Therefore if furin is used to activate VWF in vitro calcium salts are used. The most preferred calcium salt is calcium chloride.

The incubation time of furin with the immobilized VWF pro-peptide may vary depending on the system used. Also factors like temperature, buffers etc. influence the efficiency of the maturation process. However, a person skilled in the art is able to identify and to choose the most appropriate incubation time. Generally, the maturation process is terminated in less than 48 hours and already 1 min or less may be enough to produce mature VWF from its pro-form. Due to the high specificity of furin, "overactivation" of VWF (further proteolytic degradation) does not occur even after prolonged incubation time.

According to an embodiment of the invention, the incubation is performed for less than 1 min to 48 hours; in another embodiment for 10 min to 42 hours; in another embodiment for 20 min to 36 hours; and in another embodiment for 30 min to 24 hours.

The maturation process depends also on the temperature chosen in the course of the incubation. The optimal enzymatic activity of furin varies with the temperature.

According to an embodiment of the invention, the incubation is performed at a temperature of 2 to 40° C.; in another embodiment 4 to 37° C. Furin may already be efficiently active at low temperatures like 2° C. Care should be taken to select the maximum temperatures so that no or substantially no unspecific protein degradation occurs. This is generally achieved when, in one embodiment of the invention, the maximum temperatures employed are lower than 50° C.; in another embodiment, lower than 45° C.

Yet another aspect of the present invention relates to a VWF preparation obtainable from VWF pro-peptide by a method according to the present invention. The method of the present invention provides VWF, which is substantially free of VWF pro-peptide due to the high process efficiency.

Another aspect of the present invention relates to a pharmaceutical preparation comprising a VWF preparation according to the present invention. The pharmaceutical preparation can be employed in particular for treating blood coagulation diseases and can be combined with other active ingredients, such as other blood coagulation factors. Furthermore the preparation can also comprise pharmaceutically acceptable excipients, carrier and diluents.

A further aspect of the present invention relates to the use of a VWF preparation according to the present invention for the manufacture of a medicament for the treatment of von Willebrand disease (VWD).

EXAMPLES

Example 1

Calcium Dependency of Furin

Enzymatic studies on furin (Molloy S. E. et al. (1992) J. Biol. Chem. 267:16396-16402) have shown that its activity is dependent on $Ca^{2+}$ and evaluation of the crystal structure (Than et al. (2005) Acta Cryst. D61:505-512) indicate that the molecule has two binding sites for $Ca^{2+}$. Cameron et al. (Cameron A. et al. (2000) J. Biol. Chem. 275:36741-367499) described that furin required calcium concentrations of at least 1 mM for full activity with no difference in activity when the $Ca^{2+}$ concentration was increased to 50 mM. In a first set of experiments the calcium dependency of the in-house developed recombinant furin was tested and quantified. The furin was expressed from an experimental CHO clone CHO 257/1 638-25 and secreted into the cell culture medium as soluble enzyme containing a His-Tag at the C-terminus. A preparation of furin pre-purified by Ni-chelate chromatography was subjected to activity determination using a synthetic peptide Boc-Arg-Val-Arg-Arg-AMC as substrate. The VWF pro-peptide maturation reactions were performed in assay buffers containing $Ca^{2+}$ in the range between 0 and 40 mM. The results depicted in FIG. 1 confirm the literature data that the recombinant soluble furin expressed from CHO cell line shows a clear calcium dependency with maximum activity found at $Ca^{2+}$ concentrations between 0.5-1 mM but also a significant inhibition by calcium at concentrations higher than 5 mM. This inhibitory potential of calcium has to be taken into account when the source material of rVWF contains substantial amounts of $Ca^{2+}$.

Example 2

Dependency on VWF Concentration

Figure 2:
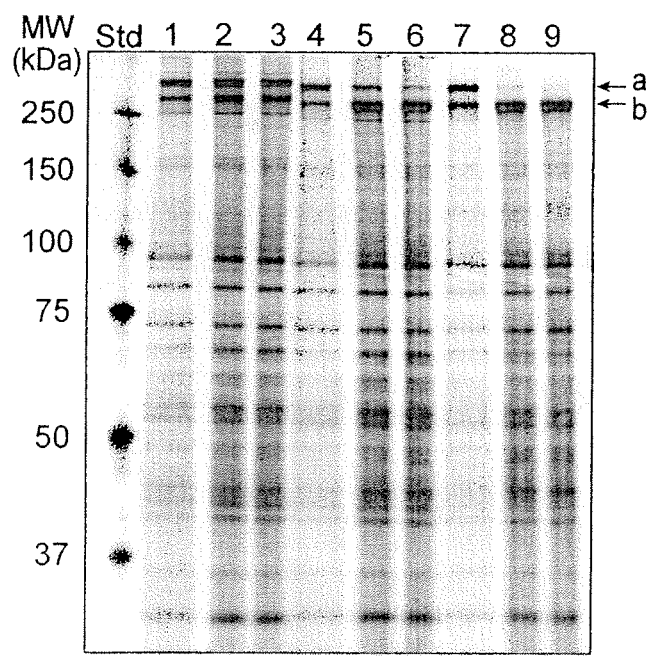
FIG. 2 shows the maturation efficacy dependence on VWF concentration. 5 ml VWF sample dissolved in resolubilization buffer (100 mM citrate, 100 mM HEPES, ph=7.0) were spiked with at 5 Units furin/U VWF and incubated for 22 h at 37° C. The samples were analyzed by SDS-PAGE on 8% gels and the separated polypeptides were visualized by silver staining.
lane 1: 1 U/ml VWF+5 U/U furin 0 h
lane 2: 5 U/ml VWF+5 U/U furin 0 h
lane 3: 10 U/ml VWF+5 U/U furin 0 h
lane 4: 1 U/ml VWF+5 U/U furin 6 h
lane 5: 5 U/ml VWF+5 U/U furin 6 h
lane 6: 10 U/ml VWF+5 U/U furin 6 h
lane 7: 1 U/ml VWF+5 U/U furin 24 h
lane 8: 5 U/ml VWF+5 U/U furin 24 h
lane 9: 10 U/ml VWF+5 U/U furin 24 h.

As deduced from classical enzyme kinetics it was considered that a higher substrate concentration could lead to a higher turn-over rate of the enzyme allowing VWF maturation at decreased furin consumption or reduced maturation time. Thus VWF maturation experiments were conducted at VWF concentrations of 1, 5 and 10 Units/ml using 5 Units furin/U VWF Ag in normalized incubation volume. The samples drawn at time points 0, 6 and 24 hours of incubation at 37° C. were analyzed by SDS-PAGE. The results shown in FIG. 2 confirm that at higher VWF concentrations the VWF maturation proceeds faster and would allow a reduced incubation time for this enzymatic step.

Figure 3:
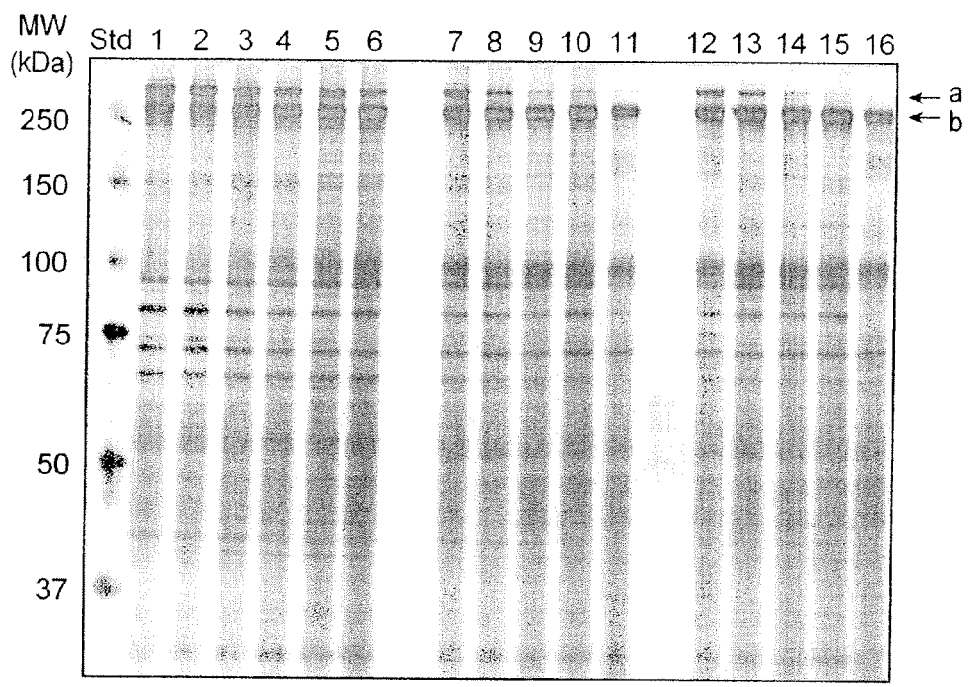
FIG. 3 shows the maturation efficacy dependence on VWF concentration. 5 ml VWF sample dissolved in resolubilization buffer (100 mM citrate, 100 mM HEPES, ph=7.0) were spiked with 0.5-4.0 Units furin/U VWF and incubated at 37° C. Samples were drawn at T=0, 20 and 24 hours. The samples were analyzed by SDS-PAGE on 8% gels and the separated polypeptides were visualized by silver staining.
lane 1: VWF 10 U/ml
lane 2: VWF+0.5 U/U furin 0 h
lane 3: VWF+1 U/U furin 0 h
lane 4: VWF+2 U/U furin 0 h
lane 5: VWF+2.5 U/U furin 0 h
lane 6: VWF+4 U/U furin 0 h lanes 7-11: as above, 20 h
lanes 12-16: as above, 24 h.

Likewise, using a concentrated VWF preparation and doing the maturation reaction with 0.5-4.0 Units furin/Unit VWF Ag at 37° C., the results indicate that a VWF maturation grade >95% can be achieved with less than 5 Units furin/Unit VWF Ag within 24 hours of incubation (see FIG. 3).

As shown by this example, the present invention further improves the furin maturation efficacy when the local concentration of the substrate VWF pro-peptide on the column is very high. Higher concentrations of VWF pro-peptide were also shown to increase the maturation velocity.

Example 3

VWF Maturation

Figure 4:
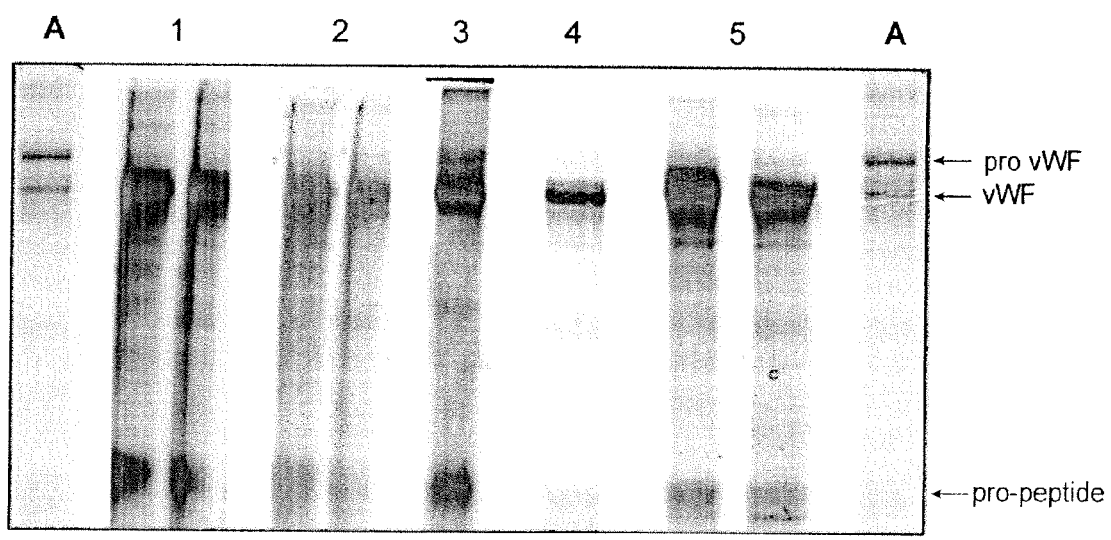
FIG. 4 shows TMAE eluates after on-column maturation. MAB flow through material containing VWF/VWF pro-peptide was pumped onto the column at approximately 180-220 Units VWF Ag/ml resin and A VWF pro-peptide/VWF before maturation
1 CR29-E1+E2 (2.4 U furin/U VWF; 3 h at 37° C.; FUR24_04_UFK_02; gradient elution
2 CR30-E1+E2 (3.2 U furin/U VWF; 1 h at 37° C.; FUR_UF06_01 (clone 488-3); gradient elution
3 CR36-E, (7.8 U furin/U VWF; 4 h at 4° C.; FUR_015 (pre-purified on TMAE), step elution
4 CR37-E, (5.8 U furin/U VWF; 8 h at 4° C.; FUR_UF06_01 (clone 488-3), batch elution
5 CR38-E1+E2 (4.8 U furin/U VWF; 8 h at 4° C.; FUR_018 (pre-purified on TMAE); gradient elution

In this example VWF pro-peptide maturation with furin is shown. Furin is contacted with VWF pro-peptide bound on a chromatography column. The chromatography step was performed on a TMAE anion exchange resin. The details of the TMAE purification step are listed in Table 1 with the buffer formulations summarized in Table 2. Applying this set-up, different procedures for the on-column maturation of bound VWF pro-peptide were investigated; including circular pumping or down-flow pumping of the furin, while concurrently varying the parameters: temperature, contact time, NaCl content and the specific furin amount. The VWF found in the eluate pool was investigated for the maturation grade by SDS-PAGE and visual evaluation of the ratio VWF pro-peptide/VWF (for example see FIG. 4).

A further parameter influencing the maturation efficacy was the quality of the furin reagent. The furin was sourced from a cell culture supernatant of a clone expressing a His-tagged furin (experimental CHO 257/1 638-25) with a low expression level and/or a clone expressing soluble furin without Tag with a high expression level. The results summarized in Table 3 show that efficient maturation at 37° C. (1 hour contact time) could be achieved with a specific furin amount of as low as 2.4 Units furin/Unit VWF Ag bound on the column. At 2-8° C. a maturation of >95% could be obtained with a specific furin amount of 3.3 Units/Unit VWF Ag at 4 hours contact time. At an ionic strength of 150 mM NaCl the overall efficacy of the on-column maturation was better compared to 90 mM NaCl, by leaving the furin unbound to the ion exchange resin at these conditions.

In Table 4a and Table 4b the impurity profile for CHO protein and furin protease activity in the eluate pool are shown in relation to parameters applied for the VWF maturation step on TMAE. The results indicate that furin concentrates from the "His-Tagged" experimental clone (low expression level) with the highest amount of additional CHO cell culture supernatant pumped over the column during maturation resulted in the highest CHO impurity levels. Data from maturation steps with furin from the GMP clone resulted in comparatively low CHO contamination levels in the eluate pools and the additional CHO cell culture volume pumped over the column was less than 2% of the volume loaded onto the column during the VWF product load. The low furin cell culture volume required for VWF pro-peptide maturation would suggest that the CHO impurity level in the eluate pool should not significantly be impacted by the furin reagent and mainly be caused by the VWF source. A similar contamination profile could be detected for the furin protease activity that behaves like a "CHO impurity".

TABLE 1

Details of the TMAE Capture/Maturation Step

| Step | Buffer | Flow rate | Column volumes |
|---|---|---|---|
| Conditioning | SIP1 | 150 cm/h | 5 |
| | WP2 | | 5 |
| | EP/WP1 | | 10 |
| Load | starting material, diluted 1:4 with water | | Appr. 200 |
| | EP/WP1 | | 5 |
| Furin treatment | FEP | | 5 |
| | Furin diluted in FDP | low | 1-10 |
| | EP/WP1 | 150 cm/h | 5 |
| Elution | Wash 20% EP3 in EP4 | | 0.5 |
| | 20% EP3-80% EP3 in EP4 | | 7 |
| | EP3 | | 10 |
| Regeneration | WP2 | | 5 |
| | SIP1 | | 5 |

TABLE 2

Buffers for the TMAE Capture/Maturation Step

| | Buffer | Formulation | pH/° C. | | Cond/° C. | |
|---|---|---|---|---|---|---|
| FEP | Furin equilibration | 50 mM HEPES, 90-150 mM NaCl, 1 mM $CaCl_2$ | 7.00 | 24.7 | 16.00 | 24.6 |
| FDP | Furin dilution buffer | 100 mM HEPES, 90-150 mM NaCl, 2 mM $CaCl_2$ | 7.00 | 26.5 | 16.25 | 26.9 |
| EP/WP1 | Equilibration/wash | 10 mM Tris, 100 mM NaAc, 86 mM NaCl | 6.50 | 25.3 | 16.62 | 25.1 |
| EP3 | Elution | 10 mM Tris, 100 mM NaAc, 200 mM NaCl | 7.52 | 23.5 | 83.4 | 23.5 |
| EP4 | Post-elution | 10 mM Tris, 100 mM NaAc, 1 M NaCl | 7.51 | 24.5 | 24.6 | 24.2 |

TABLE 2-continued

| Buffers for the TMAE Capture/Maturation Step | | | | |
|---|---|---|---|---|
| Buffer | Formulation | pH/° C. | | Cond/° C. |
| SIP1 | Base | 0.5 M NaOH | — — | — — |
| WP2 | High salt | 2 M NaCl | — — | — — |

During the on-column experiments it was observed that the performance of the step decreases significantly with the number of batches done on one column. The reason identified was column fouling due to an insufficient column regeneration procedure which included 5 CV 0.5 M NaOH and 5 CV of 2 M NaCl. The procedure was kept as it is but the base was used pre-warmed at 30-40° C. to improve the cleaning efficacy. This measure was found to be sufficient to prevent column fouling and a drop in the performance of the process step.

TABLE 3

Conditions for VWF Pro-Peptide Maturation on TMAE

| | Furin | | contact | | | | NaCl in |
|---|---|---|---|---|---|---|---|
| | Units/Unit | | time | Flow | | Temp. | Buffer |
| RunID | VWF Ag | Volume (CV) | h | ml/min | direction | ° C. | mM |
| CR02 | 14 | 6.5 | 18 | 0.06 | circular | 30-37° C. | 120 |
| CR04 | 18 | 5.8 | 2 | 3.0 | | | |
| CR05 | 11 | 5.8 | 18 | 3.0 | | | 150 |
| CR08 | 16 | 4.2 | 1 | 0.5 | downflow | | |
| CR09 | 9 | 4.2 | 1 | 0.5 | | | |
| CR21 | 26 | 2.2 | 1 | 0.4 | | | |
| CR23 | 7 | 1.1 | 1 | 0.2 | | | |
| CR24 | 6 | 1.1 | 1 | 0.2 | | | |
| CR27 | 4.7 | 1.1 | 1 | 0.2 | | | |
| CR29 | 2.4 | 3.0 | 3 | 0.5 | circular | | |
| CR30 | 3.2 | 6.4 | 1 | 1.2 | downflow | | |
| CR33 | 5.8 | 10.4 | 20 | 1.0 | circular | 2-8° C. | |
| CR34 | 6.4 | 10 | 8 | 1.0 | | | |
| CR35 | 8.2 | 4.5 | 8 | 0.5 | | | |
| CR36 | 7.8 | 4.5 | 4 | 0.5 | | | |
| CR38 | 4.8 | 3.5 | 8 | 0.5 | | | |
| CR39 | 5.9 | 3.3 | 4 | 0.5 | | | |

The VWF load on the column was always in the range of 160-180 antigen units/ml resin. After loading and washing according to Table 1 the furin VWF pro-peptide maturation followed with the parameters applied as described in the table. The last column lists the NaCl content of the diluted furin pumped through the column.

TABLE 4a

VWF Pro-Peptide On-Column Maturation; CHO and Furin Profile in the Eluate Pool

| | | | Furin treatment step | | | | |
|---|---|---|---|---|---|---|---|
| Run ID | Load [ml] | total Furin [Units] | spec. Furin amount [U/U VWF Ag] | Furin Vol. [ml] | CCS equivalent [ml] | contact time [hours] | temp. [° C.] |
| CR23 | 1646 | 11810 | 12 | 47.2 | 47 | 1 | 37 |
| CR24 | 1675 | 9383 | 6 | 6 | 392 | 1 | 37 |
| CR25 | 1923 | 18688 | 12 | 20.2 | 553 | 1 | 37 |
| CR26 | 1925 | 13980 | 9 | 16.4 | 503 | 1 | 37 |
| CR27 | 1925 | 7688 | 4.7 | 4.8 | 313 | 1 | 37 |
| CR29 | 2001 | 4040 | 2.4 | 3.3 | 215 | 1 | 37 |
| CR30 | 2001 | 5526 | 3.3 | 34.9 | 35 | 1 | 37 |
| CR33 | 2001 | 10306 | 5.8 | 77 | 77 | 20 | 4 |
| CR34 | 2001 | 11231 | 6.4 | 55 | 55 | 8 | 4 |
| CR35 | 2001 | 13387 | 8.2 | 5 | 5 | 8 | 4 |
| CR36 | 2000 | 13387 | 7.8 | 5 | 5 | 4 | 4 |
| CR38 | 2001 | 9105 | 4.8 | 2.5 | 3 | 8 | 4 |

TABLE 4b

VWF Pro-Peptide on-column maturation; CHO and Furin Profile in the Eluate Pool
Eluate pool

| Run ID | VWFAg [mg] | CHO [µg] | Specific CHO content [ug/ug VWF] | Furin [U] | Specific Furin content [U/mg VWF] | Reduction factor for furin |
|---|---|---|---|---|---|---|
| CR23 | 22.93 | 2094 | 0.091 | 1152 | 50 | 10 |
| CR24 | 17.53 | 2077 | 0.118 | 908 | 52 | 10 |
| CR25 | 12.8 | 2727 | 0.213 | 2643 | 206 | 7 |
| CR26 | 16.1 | 3417 | 0.212 | 2202 | 137 | 6 |
| CR27 | 19.1 | 1868 | 0.098 | 2700 | 141 | 3 |
| CR29 | 19.3 | 2533 | 0.131 | 1354 | 70 | 3 |
| CR30 | 22.9 | 2094 | 0.091 | 1152 | 50 | 5 |
| CR33 | 17.9 | 2334 | 0.130 | 886 | 49 | 12 |
| CR34 | 11.7 | n.d. | n.d. | 121 | 10 | 93 |
| CR35 | 20.2 | 968 | 0.048 | 671 | 33 | 20 |
| CR36 | 19.8 | 1324 | 0.067 | 817 | 41 | 16 |
| CR38 | 14.8 | n.d. | n.d. | 820 | 55 | 11 |

In Tables 4a and 4b, details of the on-column maturation experiments including the volumes of VWF/VWF pro-peptide (MAB flow through), furin concentrate and the corresponding equivalent of cell culture supernatant applied to the column are shown. The contamination profile for CHO proteins and furin protease activity in the eluate pool is shown. Run CR 24-29 used a furin concentrate of the His-Tagged experimental clone (manufactured at Pilot scale); CR30-CR33 used a furin concentrate of the GMP clone (manufactured at 10 liter fermenter scale); CR23 and CR35-CR38 used a pre-purified furin from the experimental and GMP clone, respectively.

The eluate pools were also investigated for the VWF quality in terms of additional proteolytic degradation by agarose gel electrophoresis. Additional proteolytic degradation can be nicely visualized by agarose gelelectrophoresis on 2.5% gels where the main bands of the VWF multimer structures are flanked by weak additional bands termed "satellite" bands. Western Blot results of several lots indicate no significant satellite band formation on VWF TMAE eluate pools after on-column maturation regardless of the conditions applied.

The mature VWF found in the eluate pool was analyzed for the N-terminal sequence to check if furin was using the right cleavage site under the conditions of the on-column maturation. VWF from batches CR33, CR35 and CR 36 were sequenced and the N-terminal sequence found corresponds to the expected and native sequence for mature VWF (N-term SLSCRPPMV . . . ) (SEQ ID NO: 1) further confirming the quality of the in vitro processing step.

Example 4

On-Column Maturation-Pilot Scale Implementation

The on-column maturation of VWF pro-peptide with furin was implemented at pilot scale at a 9 liter column with 30 cm diameter applying a total load of approximately 16 g VWF per batch. The process was performed at 2-8° C. with a furin maturation time of 8 hours according lab scale run CR35. The planned TMAE capture/maturation procedure for pilot scale is summarized in Table 5. For the maturation the wash 2, the activation and wash 3 was introduced after the loading, but before elution. For elution of the mature VWF the step elution was applied.

TABLE 5

TMAE Capture/Maturation Procedure at Pilot Scale

| Step | Buffer | Buffer Vol. CV | Flow rate cm/h | Time | Comment |
|---|---|---|---|---|---|
| Pre-conditioning | SIP1, WP2, EP/WP1 | 15 | 150 | 36 min | |
| Load | startin material diluted 1:4.5 (<15 mS/cm at RT) | Appr. 765 | 150 | appr. 26 h | 160-180 VWF Ag U/ml resin |
| Wash 1 | EP/WP | 5 | 150 | 12 min | |
| Wash 2 | FE1 | 5 | 150 | 12 min | 50 mM HEPES, 150 mM NaCl, 1 mM CaCl$_2$, pH = 7.0 (RT) |
| Furin Act. | Furin diluted with buffer FE1(appr. 15 mS/cm) | 2-4 | low | 8 h | Diluted with buffer FE1: 50 mM HEPES, 150 mM NaCl, 1 mM CaCl$_2$, pH = 7.0 (RT), Volume recycling appr. 4-5 times |
| Wash 3 | FE1 | 1 | 150 | 2.4 min | |
| Wash 4 | EP/WP | 5 | 150 | 12 min | |

TABLE 5-continued

TMAE Capture/Maturation Procedure at Pilot Scale

| Step | Buffer | Buffer Vol. CV | Flow rate cm/h | Time | Comment |
|---|---|---|---|---|---|
| Elution, var1 | EP1 | 20 | 75 | 96 min | |
| Elution, var2 | Gradient: 20% EP3/80% EP4 to 80% EP3/20% EP4 | 7 | 75 | 33 min | |
| Elution, var2 | EP3 | 10 | 150 | 24 min | |
| Post conditioning | WP2, SIP1, WP2, EP/WP1 | 20 | 150 | 48 | T = appr. 30° C. |

The data for 13 capture/on-column maturation steps at pilot scale are summarized in Table 6.

TABLE 6

On-column maturation at Pilot Plant scale (2100 liter load volume/batch) on a 15 l Fractogel EMD TMAE 650 column

| TMC | Load VWF Ag U/ml resin | Activity Furin/VWF U/U | Maturation Time hrs | Maturation Temperature ° C. | VWF Pro-peptide Content in Eluate poo % of VWF Ag | VWF Pro-peptide content in Load % of VWF Ag |
|---|---|---|---|---|---|---|
| ORVWTMC06006 | 124 | 0.7 | 4 | 20 | 0.64 | 49.61 |
| ORVWTMC06007 | 133 | 1.3 | 4 | 20 | 0.64 | 61.64 |
| ORVWTMC06008 | 113 | 0.7 | 4 | 20 | 0.52 | 58.62 |
| ORVWTMC06009 | 120 | 0.7 | 4 | 20 | 0.71 | 65.58 |
| ORVWTMC06010 | 144 | 2.0 | 4 | 20 | 0.64 | 55.34 |
| ORVWTMC06011 | 159 | 0.4 | 4 | 20 | 2.61 | 42.46 |
| ORVWTMC06012* | 123 | 0.1 | 4 | 20 | 8.15 | n.d. |
| ORVWTMC06013 | 128 | 0.4 | 4 | 20 | 1.88 | 43.91 |
| ORVWTMC06014 | 131 | 1.9 | 4 | 20 | 2.31 | 72.25 |
| ORVWTMC06015 | 114 | 0.8 | 4 | RT | 1.03 | 46.18 |
| ORVWTMC06016 | 123 | 0.6 | 4 | RT | 1.52 | 56.72 |
| ORVWTMC06017 | 128 | 0.7 | 4 | RT | 1.65 | 57.02 |
| ORVWTMC06018 | 143 | 0.2 | 4 | RT | 1.79 | n.d. |
| Mean | 129 | 0.9 | 4 | n.a. | 1.3 | 55.4 |
| Min | 113 | 0.2 | 4 | 20 | 0.5 | 42.5 |
| max | 159 | 2.0 | 4 | 25 | 2.6 | 72.3 |

*run not considered for statistical analyses

According to the invention, rVWF, which included rVWF pro-peptide, was treated with rfurin, though non-rfurin would also work, while it was adsorbed onto an ion exchange resin, which avoided the need to concentrate the rVWF by other means before the rfurin treatment. After appropriate dilution, the starting material was applied to the ion-exchange resin, to which rVWF adsorbed. Excess $Ca^{++}$ ions were removed by an equilibration step, and rfurin was pumped onto the column, where it resided for a given amount of time. Non-bound rfurin, VWF pro-peptide and excess CHO proteins were removed by a washing step, and rVWF was eluted from the column by an increase in ionic strength.

The data in Table 6 show that the furin maturation on-column is effective and the VWF propeptide content can be reduced from a mean of 55.4% VWF propeptide antigen in the load material to a mean of 1.3% VWF propeptide antigen of total VWF Ag in the eluate pool. The maturation level of the VWF product in the eluate pool of mean 98.7% mature VWF Ag/total VWF Ag can be achieved with a furin usage of mean 0.9 Units furin/Unit VWF antigen loaded onto the column under condition indicated in the table. At very low concentrations of rfurin (0.1 Units/Units rVWF) the maturation process resulted in a higher amount of residual VWF pro-peptide.

The invention claimed is:

1. A method for producing mature von Willebrand Factor (VWF) from von Willebrand Factor pro-peptide comprising the steps of:
   (a) immobilizing VWF pro-peptide on an ion exchange resin,
   (b) incubating the immobilized VWF pro-peptide with furin comprising activity of at least 0.2 Units furin/Unit VWF antigen (Ag) to obtain immobilized mature VWF, and
   (c) isolating at least 90% mature VWF from the ion exchange resin by elution.

2. The method according to claim 1, wherein said VWF pro-peptide is of recombinant origin.

3. The method according to claim 1, wherein said ion exchange resin comprises trimethylaminoethyl-groups (TMAE).

4. The method according to claim 1, wherein said ion exchange resin is packed in a chromatographic column.

5. The method according to claim 3, wherein said VWF pro-peptide is immobilized on the ion exchange resin and incubated with furin at a conductivity measured at 25° C. below 25 mS/cm.

6. The method according to claim 5, wherein said conductivity is below 20 mS/cm.

7. The method according to claim 5, wherein said conductivity is below 16 mS/cm.

8. The method according to claim 3, wherein said mature VWF is eluted from the ion exchange resin at a conductivity measured at 25° C. of at least 40 mS/cm.

9. The method according to claim 8 wherein said conductivity is at least 60 mS/cm.

10. The method according to claim 8 wherein said conductivity is at least 80 mS/cm.

11. The method according to claim 1, wherein said furin is comprised in a solution, which comprises further $CaCl_2$ at a concentration of 0.01 to 10 mM.

12. The method according to claim 11, wherein said $CaCl_2$ is at a concentration of 0.1 to 5 mM.

13. The method according to claim 11, wherein said $CaCl_2$ is at a concentration of 0.2 to 2 mM.

14. The method according to claim 1, wherein the incubation is performed for 1 min to 48 hours.

15. The method according to claim 14, wherein said incubation is performed for 10 min to 42 hours.

16. The method according to claim 15, wherein said incubation is performed for 20 min to 36 hours.

17. The method according to claim 16, wherein said incubation is performed for 30 min to 24 hours.

18. The method according to claim 1, wherein the incubation is performed at a temperature of 2 to 40° C.

19. The method according to claim 18, wherein said incubation is performed at a temperature of 4 to 37° C.

20. The method according to claim 1, wherein said furin is of recombinant origin.

21. The method according to claim 1 wherein the furin comprises activity of at least 0.5 Units furin/Unit VWF Ag.

22. The method according to claim 21 wherein the furin comprises activity between 0.5-4.0 Units furin/Unit VWF Ag.

23. The method according to claim 21 wherein mature VWF is at least 95% mature VWF.

24. The method according to claim 21 wherein mature VWF is at least 98% mature VWF.

25. The method according to claim 21 wherein mature VWF is at least 99% mature VWF.

26. The method according to claim 22 wherein incubating is carried out for at least 1 hour.

27. The method according to claim 26 wherein incubating is carried out at 2° C. to 8° C.

28. The method according to claim 26 wherein incubating is carried out at 37° C.

29. The method according to claim 24 wherein a mean of 0.9 Units furin/Unit VWF Ag is incubated for at least 4 hours.

30. The method according to claim 1 wherein the furin comprises activity between 0.2 to 2.0 Units furin/Unit VWF Ag for 4 hours.

* * * * *